United States Patent [19]

Berry et al.

[11] Patent Number: 5,863,765
[45] Date of Patent: Jan. 26, 1999

[54] PRODUCTION IN YEASTS OF STABLE ANTIBODY FRAGMENTS

[75] Inventors: Mark John Berry, Higham Ferrers; Paul James Davis, Felmersham; Cornelis Paul Van Der Logt, Rushden; Garry Clark Whitelam, Leicester, all of Great Britain

[73] Assignee: Quest International BV, Naarden, Netherlands

[21] Appl. No.: 894,922

[22] PCT Filed: Mar. 1, 1996

[86] PCT No.: PCT/GB96/00468

§ 371 Date: Nov. 12, 1997

§ 102(e) Date: Nov. 12, 1997

[87] PCT Pub. No.: WO96/27612

PCT Pub. Date: Sep. 12, 1996

[30] Foreign Application Priority Data

Mar. 5, 1995 [GB] United Kingdom ................ 9504344-4

[51] Int. Cl.$^6$ ............ C12P 21/00; C12N 15/13; C07K 16/46; C07H 21/04
[52] U.S. Cl. ............ 435/69.1; 435/255.1; 530/387.3; 536/23.53
[58] Field of Search ............... 435/69.1, 255.1; 530/387.3; 536/23.53

*Primary Examiner*—James Ketter
*Assistant Examiner*—William Sandals
*Attorney, Agent, or Firm*—Pillsbury Madison & Sutro LLP

[57] ABSTRACT

Associative portions of antibody light and heavy chains, especially Fv fragments, are expressed in a transformed organism as a single peptide chain connected by a linking peptide. This is cleaved, possibly while peptide synthesis is incomplete, by an enzyme of the transformed organism which is expressing the single peptide. This ensures production of both chains in equal amounts, but produces them as separate chains which are free to associate and fold.

13 Claims, 9 Drawing Sheets

Fig 7:
Cloning Strategy
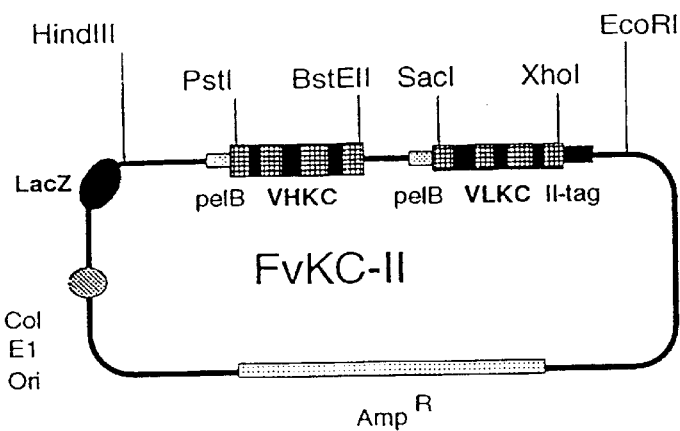
a)
remove BstEII/SacI fragment
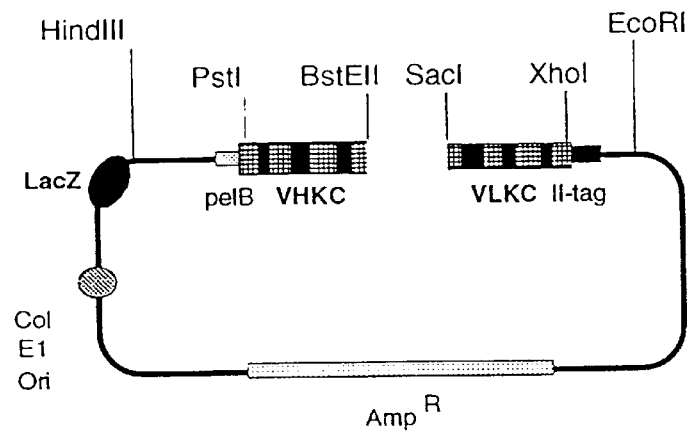
b)
insert synthetic BstEII/SacI fragment encoding KEX2 site (Oligo.1 + Oligo.2)
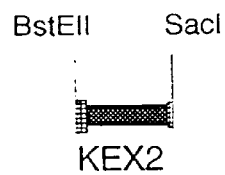
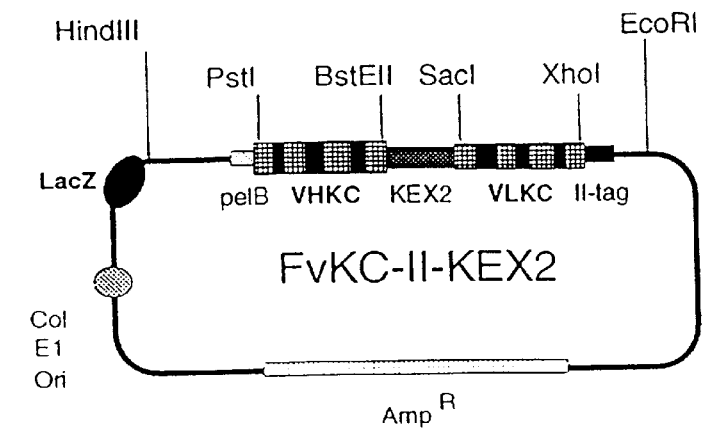
c)

Cloning Strategy pelB leader

```
                                                    M  K  Y  L  P  T
AAGCTTGCATGCAAATTCTATTTCAAGGAGACAGTCATAATGAAATACCTATTGCCTACG
 A  A  A  G  L  L  L  L  A  A  Q  P  A  M  A  Q  V  Q  L  Q
GCAGCCGCTGGATTGTTATTACTCGCTGCCCAACCGGCCATGGCCCAGGTGCAGCTGCAG
```

```
 Q  S  G  A  E  L  V  K  P  G  P  S  V  K  L  S  C  K  A  S
CAGTCTGGGGCTGAACTGGTGAAGCCTGGGCCTTCTGTGAAGCTGTCCTGCAAGGCTTCC
 D  Y  T  F  T  S  Y  W  M  H  W  V  K  Q  R  P  G  Q  G  L
GACTACACCTTCACCAGTTATTGGATGCACTGGGTGAAGCAGAGGCCTGGACAAGGCCTT
```

VHKC

```
 E  W  I  G  E  I  N  P  T  N  G  R  T  Y  Y  N  E  K  F  K
GAGTGGATTGGAGAGATTAATCCTACCAACGGTCGTACTTATTACAATGAGAAGTTCAAG
 S  K  A  T  L  T  V  D  K  S  S  S  T  A  Y  M  Q  L  S  S
AGCAAGGCCACACTGACTGTAGACAAATCTTCCAGTACAGCCTACATGCAGCTCAGCAGC
 L  T  S  E  D  S  A  V  Y  Y  C  A  R  R  Y  G  N  S  F  D
CTGACATCTGAGGACTCTGCGGTCTATTACTGTGCAAGACGGTATGGTAACTCCTTTGAC
 Y  W  G  Q  G  T  T  V  T  V  S  S
TACTGGGGCCAAGGGACCACGGTCACCGTCTCCTCATAATAAGAGCTATGGGAGCTTGCA
``` pelB leader

```
                                             M  K  Y  L  L  P  T  A  A  A
TGCAAATTCTATTTCAAGGAGACAGTCATAATGAAATACCTATTGCCTACGGCAGCCGCT
 G  L  L  L  A  A  Q  P  A  M  A  D  I  E  L  T  Q  S  P
GGATTGTTATTACTCGCTGCCCAACCAGCGATGGCCGACATCGAGCTCACCCAGTCTCCA
```

```
 D  S  L  A  V  S  L  G  Q  R  A  T  I  S  C  R  A  S  E  S
GATTCTTTGGCTGTGTCTCTAGGGCAGAGGGCCACCATATCCTGCAGAGCCAGTGAAAGT
 V  D  S  Y  G  N  S  F  M  Q  W  Y  Q  Q  K  P  G  Q  P  P
GTTGATAGTTATGGCAATAGTTTTATGCAGTGGTACCAGCAGAAACCAGGACAGCCACCC
```

VLKC

```
 K  L  L  I  Y  R  A  S  N  L  E  S  G  I  P  A  R  F  S  G
AAACTCCTCATCTATCGTGCATCCAACCTAGAATCTGGGATTCCTGCCAGGTTCAGTGGC
 T  G  S  R  T  D  F  T  L  T  I  N  P  V  E  A  D  D  V  A
ACTGGGTCTAGGACAGACTTCACCCTCACCATTAATCCTGTGGAGGCTGATGATGTTGCA
 T  Y  Y  C  Q  Q  S  D  E  Y  P  Y  M  Y  T  F  G  G  G  T
ACCTATTATTGTCAACAAAGTGATGAGTATCCGTACATGTACACGTTCGGAGGGGGGACC
```

Hydrophil II tag

```
 K  L  E  I  K  R  G  S  G  S  G  N  S  G  K  G  Y  L  K
AAGCTCGAGATCAAACGGGGATCCGGTAGCGGGAACTCCGGTAAGGGGTACCTGAAGTAA
```

```
TAAGATCAAACGGTAATAAGGATCCAGCTCGAATTC
```

Fig 8: FvKC-II pelB leader

AAGCTTGCATGCAAATTCTATTTCAAGGAGACAGTCATAATGAAATACCTATTGCCTACG
M K Y L L P T

GCAGCCGCTGGATTGTTATTACTCGCTGCCCAACCGGCCATGGCCCAGGTGCAGCTGCAG
A A A G L L L L A A Q P A M A Q V Q L Q

CAGTCTGGGGCTGAACTGGTGAAGCCTGGGCCTTCTGTGAAGCTGTCCTGCAAGGCTTCC
Q S G A E L V K P G P S V K L S C K A S

GACTACACCTTCACCAGTTATTGGATGCACTGGGTGAAGCAGAGGCCTGGACAAGGCCTT
D Y T F T S Y W M H W V K Q R P G Q G L

VHKC

GAGTGGATTGGAGAGATTAATCCTACCAACGGTCGTACTTATTACAATGAGAAGTTCAAG
E W I G E I N P T N G R T Y Y N E K F K

AGCAAGGCCACACTGACTGTAGACAAATCTTCCAGTACAGCCTACATGCAGCTCAGCAGC
S K A T L T V D K S S S T A Y M Q L S S

CTGACATCTGAGGACTCTGCGGTCTATTACTGTGCAAGACGGTATGGTAACTCCTTTGAC
L T S E D S A V Y Y C A R R Y G N S F D

KEX2 site

TACTGGGGCCAAGGGACCACGGTCACCGTCTCCTCACGAATGGATAAAAGGGACATCGAG
Y W G Q G T T V T V S S R M D K R D I E

CTCACCCAGTCTCCAGATTCTTTGGCTGTGTCTCTAGGGCAGAGGGCCACCATATCCTGC
L T Q S P D S L A V S L G Q R A T I S C

AGAGCCAGTGAAAGTGTTGATAGTTATGGCAATAGTTTTATGCAGTGGTACCAGCAGAAA
R A S E S V D S Y G N S F M Q W Y Q Q K

CCAGGACAGCCACCCAAACTCCTCATCTATCGTGCATCCAACCTAGAATCTGGGATTCCT
P G Q P P K L L I Y R A S N L E S G I P

VLKC

GCCAGGTTCAGTGGCACTGGGTCTAGGACAGACTTCACCCTCACCATTAATCCTGTGGAG
A R F S G T G S R T D F T L T I N P V E

GCTGATGATGTTGCAACCTATTATTGTCAACAAAGTGATGAGTATCCGTACATGTACACG
A D D V A T Y Y C Q Q S D E Y P Y M Y T

Hydrophil II tag

TTCGGAGGGGGGACCAAGCTCGAGATCAAACGGGGATCCGGTAGCGGGAACTCCGGTAAG
F G G G T K L E I K R G S G S G N S G K

GGGTACCTGAAGTAATAAGATCAAACGGTAATAAGGATCCAGCTCGAATTC
G Y L K

Fig 9: FvKC-II-KEX2

SnaBI site

```
                                                  A  Y  V  Q  V  Q  L  Q
                                             AAGCTTACGTACAGGTGCAGCTGCAG
         Q  S  G  A  E  L  V  K  P  G  P  S  V  K  L  S  C  K  A  S
         CAGTCTGGGGCTGAACTGGTGAAGCCTGGGCCTTCTGTGAAGCTGTCCTGCAAGGCTTCC

D  Y  T  F  T  S  Y  W  M  H  W  V  K  Q  R  P  G  Q  G  L
         GACTACACCTTCACCAGTTATTGGATGCACTGGGTGAAGCAGAGGCCTGGACAAGGCCTT
```

VHKC
```
         E  W  I  G  E  I  N  P  T  N  G  R  T  Y  Y  N  E  K  F  K
         GAGTGGATTGGAGAGATTAATCCTACCAACGGTCGTACTTATTACAATGAGAAGTTCAAG

S  K  A  T  L  T  V  D  K  S  S  S  T  A  Y  M  Q  L  S  S
         AGCAAGGCCACACTGACTGTAGACAAATCTTCCAGTACAGCCTACATGCAGCTCAGCAGC

L  T  S  E  D  S  A  V  Y  Y  C  A  R  R  Y  G  N  S  F  D
         CTGACATCTGAGGACTCTGCGGTCTATTACTGTGCAAGACGGTATGGTAACTCCTTTGAC
```

KEX2 site
```
         Y  W  G  Q  G  T  T  V  T  V  S  S  R  M  D  K  R  D  I  E
         TACTGGGGCCAAGGGACCACGGTCACCGTCTCCTCACGAATGGATAAAAGGGACATCGAG L  T  Q  S  P  D  S  L  A  V  S  L  G  Q  R  A  T  I  S  C
         CTCACCCAGTCTCCAGATTCTTTGGCTGTGTCTCTAGGGCAGAGGGCCACCATATCCTGC R  A  S  E  S  V  D  S  Y  G  N  S  F  M  Q  W  Y  Q  Q  K
         AGAGCCAGTGAAAGTGTTGATAGTTATGGCAATAGTTTTATGCAGTGGTACCAGCAGAAA P  G  Q  P  P  K  L  L  I  Y  R  A  S  N  L  E  S  G  I  P
         CCAGGACAGCCACCCAAACTCCTCATCTATCGTGCATCCAACCTAGAATCTGGGATTCCT
```

VLKC
```
         A  R  F  S  G  T  G  S  R  T  D  F  T  L  T  I  N  P  V  E
         GCCAGGTTCAGTGGCACTGGGTCTAGGACAGACTTCACCCTCACCATTAATCCTGTGGAG

A  D  D  V  A  T  Y  Y  C  Q  Q  S  D  E  Y  P  Y  M  Y  T
         GCTGATGATGTTGCAACCTATTATTGTCAACAAAGTGATGAGTATCCGTACATGTACACG

F  G  G  G  T  K  L  E  I  K  R  G  S  G  S  G  N  S  G  K
         TTCGGAGGGGGGACCAAGCTCGAGATCAAACGGGGATCCGGTAGCGGGAACTCCGGTAAG
```
Hydrophil II tag
```
         G  Y  L  K
         GGGTACCTGAAGTAATAAGATCAAACGGTAATAAGGATCCAGCTGAATTC
```

Fig 10: Yeast-FvKC-II-KEX2

Fig 11: Recovery of FvKC-II from *Pichia*

[Chromatogram with x-axis "Elution volume" and y-axis "Absorbance (280nm)". Labeled arrows indicate: Load sample, Wash PBS, Wash 1M NaCl, Elute 50mM glycine, pH 2.2. Fraction 1 and Fraction 2 are indicated at the final elution peak.]

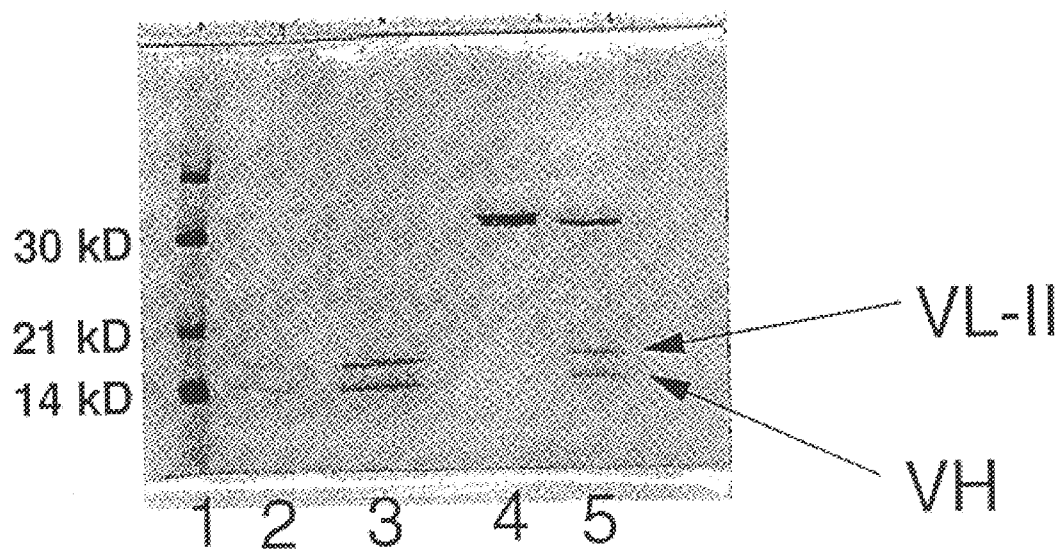
Fig 12: SDS-PAGE analysis of FvKC-II produced in *Pichia*

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

CGAATGGATA AAAGG                                                              1 5

( 2 ) INFORMATION FOR SEQ ID NO:2:

( i ) SEQUENCE CHARACTERISTICS:
        ( A ) LENGTH: 5 amino acids (B) TYPE: amino acid
(D) TOPOLOGY: linear (ii) MOLECULE TYPE: peptide (iii) HYPOTHETICAL:

(xi) SEQUENCE DESCRIPTION: SEQ ID NO:2:

Arg Met Asp Lys Arg
1               5

(2) INFORMATION FOR SEQ ID NO:3:

(i) SEQUENCE CHARACTERISTICS:
    (A) LENGTH: 13 amino acids
    (B) TYPE: amino acid
    (D) TOPOLOGY: linear (ii) MOLECULE TYPE: peptide (xi) SEQUENCE DESCRIPTION: SEQ ID NO:3:

Gly Ser Gly Ser Gly Asn Ser Gly Lys Gly Tyr Leu Lys
1               5                   10

(2) INFORMATION FOR SEQ ID NO:4:

(i) SEQUENCE CHARACTERISTICS:
    (A) LENGTH: 996 base pairs
    (B) TYPE: nucleic acid
    (C) STRANDEDNESS: double
    (D) TOPOLOGY: circular (ii) MOLECULE TYPE: DNA (xi) SEQUENCE DESCRIPTION: SEQ ID NO:4:

| | | | | | | |
|---|---|---|---|---|---|---|
| AAGCTTGCAT | GCAAATTCTA | TTTCAAGGAG | ACAGTCATAA | TGAAATACCT | ATTGCCTACG | 60 |
| GCAGCCGCTG | GATTGTTATT | ACTCGCTGCC | CAACCGGCCA | TGGCCCAGGT | GCAGCTGCAG | 120 |
| CAGTCTGGGG | CTGAACTGGT | GAAGCCTGGG | CCTTCTGTGA | AGCTGTCCTG | CAAGGCTTCC | 180 |
| GACTACACCT | TCACCAGTTA | TTGGATGCAC | TGGGTGAAGC | AGAGGCCTGG | ACAAGGCCTT | 240 |
| GAGTGGATTG | GAGAGATTAA | TCCTACCAAC | GGTCGTACTT | ATTACAATGA | GAAGTTCAAG | 300 |
| AGCAAGGCAA | CACTGACTGT | AGACAAATCT | TCCAGTACAG | CCTACATGCA | GCTCAGCAGC | 360 |
| CTGACATCTG | AGGACTCTGC | GGTCTATTAC | TGTGCAAGAC | GGTATGGTAA | CTCCTTTGAC | 420 |
| TACTGGGGCC | AAGGGACCAC | GGTCACCGTC | TCCTCATAAT | AAGAGCTATG | GGAGCTTGCA | 480 |
| TGCAAATTCT | ATTTCAAGGA | GACAGTCATA | ATGAAATACC | TATTGCCTAC | GGCAGCCGCT | 540 |
| GGATTGTTAT | TACTCGCTGC | CCAACCAGCG | ATGGCCGACA | TCGAGCTCAC | CCAGTCTCCA | 600 |
| GATTCTTTGG | CTGTGTCTCT | AGGGCAGAGG | GCCACCATAT | CCTGCAGAGC | CAGTGAAAGT | 660 |
| GTTGATAGTT | ATGGCAATAG | TTTTATGCAG | TGGTACCAGC | AGAAACCAGG | ACAGCCACCC | 720 |
| AAACTCCTCA | TCTATCGTGC | ATCCAACCTA | GAATCTGGGA | TTCCTGCCAG | GTTCAGTGGC | 780 |
| ACTGGGTCTA | GGACAGACTT | CACCCTCACC | ATTAATCCTG | TGGAGGCTGA | TGATGTTGCA | 840 |
| ACCTATTATT | GTCAACAAAG | TGATGAGTAT | CCGTACATGT | ACACGTTCGG | AGGGGGGACC | 900 |
| AAGCTCGAGA | TCAAACGGGG | ATCCGGTAGC | GGGAACTCCG | GTAAGGGGTA | CCTGAAGTAA | 960 |
| TAAGATCAAA | CGGTAATAAG | GATCCAGCTC | GAATTC | | | 996 |

(2) INFORMATION FOR SEQ ID NO:5:

(i) SEQUENCE CHARACTERISTICS:
    (A) LENGTH: 139 amino acids
    (B) TYPE: amino acid (D) TOPOLOGY: linear (ii) MOLECULE TYPE: protein (xi) SEQUENCE DESCRIPTION: SEQ ID NO:5:

| Met | Lys | Tyr | Leu | Leu | Pro | Thr | Ala | Ala | Ala | Gly | Leu | Leu | Leu | Leu | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ala | Gln | Pro | Ala | Met | Ala | Gln | Val | Gln | Leu | Gln | Gln | Ser | Gly | Ala | Glu |
|-----|-----|-----|-----|-----|-----|-----|-----|-----|-----|-----|-----|-----|-----|-----|-----|
|     |     |     | 20  |     |     |     | 25  |     |     |     |     | 30  |     |     |     |

| Leu | Val | Lys | Pro | Gly | Pro | Ser | Val | Lys | Leu | Ser | Cys | Lys | Ala | Ser | Asp |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Tyr | Thr | Phe | Thr | Ser | Tyr | Trp | Met | His | Trp | Val | Lys | Gln | Arg | Pro | Gly |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Gln | Gly | Leu | Glu | Trp | Ile | Gly | Glu | Ile | Asn | Pro | Thr | Asn | Gly | Arg | Thr |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Tyr | Tyr | Asn | Glu | Lys | Phe | Lys | Ser | Lys | Ala | Thr | Leu | Thr | Val | Asp | Lys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ser | Ser | Ser | Thr | Ala | Tyr | Met | Gln | Leu | Ser | Ser | Leu | Thr | Ser | Glu | Asp |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Ser | Ala | Val | Tyr | Tyr | Cys | Ala | Arg | Arg | Tyr | Gly | Asn | Ser | Phe | Asp | Tyr |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Trp | Gly | Gln | Gly | Thr | Thr | Val | Thr | Val | Ser | Ser |
|-----|-----|-----|-----|-----|-----|-----|-----|-----|-----|-----|
|     |     |     | 130 |     |     |     | 135 |     |     |     |

(2) INFORMATION FOR SEQ ID NO:6:

(i) SEQUENCE CHARACTERISTICS:
(A) LENGTH: 149 amino acids
(B) TYPE: amino acid
(D) TOPOLOGY: linear (ii) MOLECULE TYPE: protein (xi) SEQUENCE DESCRIPTION: SEQ ID NO:6:

| Met | Lys | Tyr | Leu | Leu | Pro | Thr | Ala | Ala | Ala | Gly | Leu | Leu | Leu | Leu | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ala | Gln | Pro | Ala | Met | Ala | Asp | Ile | Glu | Leu | Thr | Gln | Ser | Pro | Asp | Ser |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Leu | Ala | Val | Ser | leu | Gly | Gln | Arg | Ala | Thr | Ile | Ser | Cys | Arg | Ala | Ser |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Glu | Ser | Val | Asp | Ser | Tyr | Gly | Asn | Ser | Phe | Met | Gln | Trp | Tyr | Gln | Gln |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Lys | Pro | Gly | Gln | Pro | Pro | Lys | Leu | Leu | Ile | Tyr | Arg | Ala | Ser | Asn | Leu |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Glu | Ser | Gly | Ile | Pro | Ala | Arg | Phe | Ser | Gly | Thr | Gly | Ser | Arg | Thr | Asp |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Phe | Thr | Leu | Thr | Ile | Asn | Pro | Val | Glu | Ala | Asp | Asp | Val | Ala | Thr | Tyr |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Tyr | Cys | Gln | Gln | Ser | Asp | Glu | Tyr | Pro | Tyr | Met | Tyr | Thr | Phe | Gly | Gly |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Gly | Thr | Lys | Leu | Glu | Ile | Lys | Arg | Gly | Ser | Gly | Ser | Gly | Asn | Ser | Gly |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Lys | Gly | Tyr | Leu | Lys |
|-----|-----|-----|-----|-----|
| 145 |     |     |     |     |

(2) INFORMATION FOR SEQ ID NO:7:

(i) SEQUENCE CHARACTERISTICS:
(A) LENGTH: 41 base pairs (B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:7:

GTCACCGTCT CCTCACGAAT GGATAAAAGG GACATCGAGC T          41

(2) INFORMATION FOR SEQ ID NO:8:

(i) SEQUENCE CHARACTERISTICS:
  (A) LENGTH: 32 base pairs
  (B) TYPE: nucleic acid
  (C) STRANDEDNESS: single
  (D) TOPOLOGY: linear (ii) MOLECULE TYPE: DNA (xi) SEQUENCE DESCRIPTION: SEQ ID NO:8:

CGATGTCCCT TTTATCCATT CGTGAGGAGA CG          32

(2) INFORMATION FOR SEQ ID NO:9:

(i) SEQUENCE CHARACTERISTICS:
  (A) LENGTH: 891 base pairs
  (B) TYPE: nucleic acid
  (C) STRANDEDNESS: double
  (D) TOPOLOGY: circular (ii) MOLECULE TYPE: DNA (xi) SEQUENCE DESCRIPTION: SEQ ID NO:9:

AAGCTTGCAT GCAAATTCTA TTTCAAGGAG ACAGTCATAA TGAAATACCT ATTGCCTAGG    60
GCAGCCGCTG GATTGTTATT ACTCGCTGCC CAACCGGCCA TGGCCCAGGT GCAGCTGCAG   120
CAGTCTGGGG CTGAACTGGT GAAGCCTGGG CCTTCTGTGA AGCTGTCCTG CAAGGCTTCC   180
GACTACACCT TCACCAGTTA TTGGATGCAC TGGGTGAAGC AGAGGCCTGG ACAAGGCCTT   240
GAGTGGATTG GAGAGATTAA TCCTACCAAC GGTCGTACTT ATTACAATGA GAAGTTCAAG   300
AGCAAGGCCA CACTGACTGT AGACAAATCT TCCAGTACAG CCTACATGCA GCTCAGCAGC   360
CTGACATCTG AGGACTCTGC GGTCTATTAC TGTGCAAGAC GGTATGGTAA CTCCTTTGAC   420
TACTGGGGCC AAGGGACCAC GGTCACCGTC TCCTCACGAA TGGATAAAAG GACATCGAG   480
CTCACCCAGT CTCCAGATTC TTTGGCTGTG TCTCTAGGGC AGAGGGCCAC CATATCCTGC   540
AGAGCCAGTG AAAGTGTTGA TAGTTATGGC AATAGTTTTA TGCAGTGGTA CCAGCAGAAA   600
CCAGGACAGC CACCCAAACT CCTCATCTAT CGTGCATCCA ACCTAGAATC TGGGATTCTT   660
GCCAGGTTCA GTGGCACTGG GTCTAGGACA GACTTCACCC TCACCATTAA TCCTGTGGAG   720
GCTGATGATG TTGCAACCTA TTATTGTCAA CAAAGTGATG AGTATCCGTA CATGTACACG   780
TTCGGAGGGG GGACCAAGCT CGAGATCAAA CGGGGATCCG GTAGCGGGAA CTCCGGTAAG   840
GGGTACCTGA AGTAATAAGA TCAAACGGTA ATAAGGATCC AGCTCGAATT C           891

(2) INFORMATION FOR SEQ ID NO:10:

(i) SEQUENCE CHARACTERISTICS:
  (A) LENGTH: 271 amino acids
  (B) TYPE: amino acid
  (D) TOPOLOGY: linear (ii) MOLECULE TYPE: protein (xi) SEQUENCE DESCRIPTION: SEQ ID NO:10:

```
Met  Lys  Tyr  Leu  Leu  Pro  Thr  Ala  Ala  Ala  Gly  Leu  Leu  Leu  Leu  Ala
1              5                        10                       15

Ala  Gln  Pro  Ala  Met  Ala  Gln  Val  Gln  Leu  Gln  Gln  Ser  Gly  Ala  Glu
               20                  25                       30

Leu  Val  Lys  Pro  Gly  Pro  Ser  Val  Lys  Leu  Ser  Cys  Lys  Ala  Ser  Asp
          35                       40                  45

Tyr  Thr  Phe  Thr  Ser  Tyr  Trp  Met  His  Trp  Val  Lys  Gln  Arg  Pro  Gly
     50                       55                  60

Gln  Gly  Leu  Glu  Trp  Ile  Gly  Glu  Ile  Asn  Pro  Thr  Asn  Gly  Arg  Thr
65                       70                  75                            80

Tyr  Tyr  Asn  Glu  Lys  Phe  Lys  Ser  Lys  Ala  Thr  Leu  Thr  Val  Asp  Lys
               85                       90                            95

Ser  Ser  Ser  Thr  Ala  Tyr  Met  Gln  Leu  Ser  Ser  Leu  Thr  Ser  Glu  Asp
               100                      105                      110

Ser  Ala  Val  Tyr  Tyr  Cys  Ala  Arg  Arg  Tyr  Gly  Asn  Ser  Phe  Asp  Tyr
          115                      120                      125

Trp  Gly  Gln  Gly  Thr  Thr  Val  Thr  Val  Ser  Ser  Arg  Met  Asp  Lys  Arg
     130                      135                      140

Asp  Ile  Glu  Leu  Thr  Gln  Ser  Pro  Asp  Ser  Leu  Ala  Val  Ser  Leu  Gly
145                      150                      155                       160

Gln  Arg  Ala  Thr  Ile  Ser  Cys  Arg  Ala  Ser  Glu  Ser  Val  Asp  Ser  Tyr
               165                           170                 175

Gly  Asn  Ser  Phe  Met  Gln  Trp  Tyr  Gln  Gln  Lys  Pro  Gly  Gln  Pro  Pro
               180                      185                      190

Lys  Leu  Leu  Ile  Tyr  Arg  Ala  Ser  Asn  Leu  Glu  Ser  Gly  Ile  Pro  Ala
          195                      200                      205

Arg  Phe  Ser  Gly  thr  Gly  Ser  Arg  Thr  Asp  Phe  Thr  Leu  Thr  Ile  Asn
     210                      215                      220

Pro  Val  Glu  Ala  Asp  Asp  Val  Ala  Thr  Tyr  Tyr  Cys  Gln  Gln  Ser  Asp
225                      230                      235                       240

Glu  Tyr  Pro  Tyr  Met  Tyr  Thr  Phe  Gly  Gly  Gly  Thr  Lys  Leu  Glu  Ile
               245                      250                      255

Lys  Arg  Gly  Ser  Gly  Ser  Gly  Asn  Ser  Gly  Lys  Gly  Tyr  Leu  Lys
               260                      265                      270
```

( 2 ) INFORMATION FOR SEQ ID NO:11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

AGCTTACGTA CAGGTGCAGC TGCA          24

( 2 ) INFORMATION FOR SEQ ID NO:12:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

GCTGCACCTG TACGTA          16

( 2 ) INFORMATION FOR SEQ ID NO:13:

( i ) SEQUENCE CHARACTERISTICS:
        ( A ) LENGTH: 797 base pairs
        ( B ) TYPE: nucleic acid
        ( C ) STRANDEDNESS: double
        ( D ) TOPOLOGY: circular ( i i ) MOLECULE TYPE: DNA ( x i ) SEQUENCE DESCRIPTION: SEQ ID NO:13:

```
AAGCTTACGT ACAGGTGCAG CTGCAGCAGT CTGGGGCTGA ACTGGTGAAG CCTGGGCCTT      60
CTGTGAAGCT GTCCTGCAAG GCTTCCGACT ACACCTTCAC CAGTTATTGG ATGCACTGGG     120
TGAAGCAGAG GCCTGGACAA GGCCTTGAGT GGATTGGAGA GATTAATCCT ACCAACGGTC     180
GTACTTATTA CAATGAGAAG TTCAAGAGCA AGGCCACACT GACTGTAGAC AAATCTTCCA     240
GTACAGCCTA CATGCAGCTC AGCAGCCTGA CATCTGAGGA CTCTGCGGTC TATTACTGTG     300
CAAGACGGTA TGGTAACTCC TTTGACTACT GGGGCCAAGG GACCACGGTC ACCGTCTCCT     360
CACGAATGGA TAAAAGGGAC ATCGAGCTCA CCCAGTCTCC AGATTCTTTG GCTGTGTCTC     420
TAGGGCAGAG GGCCACCATA TCCTGCAGAG CCAGTGAAAG TGTTGATAGT TATGGCAATA     480
GTTTTATGCA GTGGTACCAG CAGAAACCAG GACAGCCACC CAAACTCCTC ATCTATCGTG     540
CATCCAACCT AGAATCTGGG ATTCCTGCCA GGTTCAGTGG CACTGGGTCT AGGACAGACT     600
TCACCCTCAC CATTAATCCT GTGGAGGCTG ATGATGTTGC AACCTATTAT TGTCAACAAA     660
GTGATGAGTA TCCGTACATG TACACGTTCG GAGGGGGGAC CAAGCTCGAG ATCAAACGGG     720
GATCCGGTAG CGGGAACTCC GGTAAGGGGT ACCTGAAGTA ATAAGATCAA ACGGTAATAA     780
GGATCCAGCT CGAATTC                                                   797
```

( 2 ) INFORMATION FOR SEQ ID NO:14:

( i ) SEQUENCE CHARACTERISTICS:
        ( A ) LENGTH: 252 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Ala Tyr Val Gln Val Gln Leu Gln Gln Ser Gly Ala Glu Leu Val Lys
 1               5                  10                  15

Pro Gly Pro Ser Val Lys Leu Ser Cys Lys Ala Ser Asp Tyr Thr Phe
            20                  25                  30

Thr Ser Tyr Trp Met His Trp Val Lys Gln Arg Pro Gly Gln Gly Leu
        35                  40                  45

Glu Trp Ile Gly Glu Ile Asn Pro Thr Asn Gly Arg Thr Tyr Tyr Asn
    50                  55                  60

Glu Lys Phe Lys Ser Lys Ala Thr Leu Thr Val Asp Lys Ser Ser Ser
65                  70                  75                  80

Thr Ala Tyr Met Gln Leu Ser Ser Leu Thr Ser Glu Asp Ser Ala Val
                85                  90                  95

Tyr Tyr Cys Ala Arg Arg Tyr Gly Asn Ser Phe Asp Tyr Trp Gly Gln
            100                 105                 110

Gly Thr Thr Val Thr Val Ser Ser Arg Met Asp Lys Arg Asp Ile Glu
        115                 120                 125

Leu Thr Gln Ser Pro Asp Ser Leu Ala Val Ser Leu Gly Gln Arg Ala
    130                 135                 140
```

| | | | | | | | | | | | | | | | |
|---|---|---|---|---|---|---|---|---|---|---|---|---|---|---|---|
| Thr 145 | Ile | Ser | Cys | Arg | Ala 150 | Ser | Glu | Ser | Val | Asp 155 | Ser | Tyr | Gly | Asn | Ser 160 |
| Phe | Met | Gln | Trp | Tyr 165 | Gln | Gln | Lys | Pro | Gly 170 | Gln | Pro | Pro | Lys | Leu 175 | Leu |
| Ile | Tyr | Arg | Ala 180 | Ser | Asn | Leu | Glu | Ser 185 | Gly | Ile | Pro | Ala | Arg 190 | Phe | Ser |
| Gly | Thr | Gly 195 | Ser | Arg | Thr | Asp | Phe 200 | Thr | Leu | Thr | Ile | Asn 205 | Pro | Val | Glu |
| Ala | Asp 210 | Asp | Val | Ala | Thr | Tyr 215 | Tyr | Cys | Gln | Gln | Ser 220 | Asp | Glu | Tyr | Pro |
| Tyr 225 | Met | Tyr | Thr | Phe | Gly 230 | Gly | Gly | Thr | Lys | Leu 235 | Glu | Ile | Lys | Arg | Gly 240 |
| Ser | Gly | Ser | Gly | Asn 245 | Ser | Gly | Lys | Gly | Tyr 250 | Leu | Lys | | | | |

PRODUCTION IN YEASTS OF STABLE ANTIBODY FRAGMENTS

This invention relates to the production of antibody fragments and analogous entities. In recent years there has been considerable interest in the production of antibody fragments. One fragment of particular interest is the so-called Fv fragment which consists of the variable domain of the light chain of an antibody and the associated variable domain of the antibody's heavy chain. The inter-molecular forces which bring about the association of these domains in whole antibodies also hold them together in an Fv fragment.

The individual domains of an Fv fragment can each be expressed by a genetically transformed organism. Once they are present together in solution they will spontaneously associate to give the desired Fv fragment.

The expression of single antibody domains by a transformed microorganism is discussed at length in European Patent 368684 (Medical Research Council).

If the required variable domains from the light and heavy chains are present together in solution they will in general spontaneously associate together into the required Fv fragments; association is particularly favoured by a high concentration of the domains. It is not however straightforward to get both of the variable domains produced and in solution together in equal amounts and in appropriate concentrations which favour association. One possibility is to express them both by means of separate host organisms and then bring them together. This, however, requires the transformation of two host organisms and the amounts of the variable domains which are expressed may not match each other. Moreover, it is generally thought that the expression of the heavy chain without the light chain is often harmful to the cells which express it, making it difficult to obtain concentrations suitable for industrial production.

Another possibility is to transform a host organism so that a single transformed organism contains genetic information coding for both variable domains. This can be achieved by assembling the genetic information coding for both domains on a single vector as disclosed by Reichmann et al, J. Mol. Biol. 203 825 [1988]. However, in this case the host organism may not express the two variable domains in equal amounts, thereby wasting cellular metabolism in unproductive synthesis, and again risking harm to the cells from the surplus of one chain.

A way around the difficulties is proposed in European Patent 281604B which discloses the production of a single polypeptide containing the binding portion of each variable domain along with a linking peptide sequence which joins them together. This linking peptide sequence is designed so that after the single polypeptide has been expressed, the binding portions of the two variable domains can associate together to form a molecule analogous to an Fv fragment which is the so-called single chain Fv fragment. European Patent 281604B brings two key advantages. First, the two domains are produced in equal quantities. Secondly, the two domains are produced at high "local" concentration—since they are linked—and therefore association is strongly favoured.

It is explained in this prior document that the design of this single polypeptide molecule necessitates some compromise. It is taught that the linking region should extend from the C-terminal region of the light chain to the N-terminal region of the heavy chain. However it should not join the extremities of these terminal regions because they are relatively far apart in a natural antibody, (and likewise in a complete Fv fragment).

Instead the peptide link should extend from a point spaced somewhat inwardly from the C-terminal of the light chain to a point spaced somewhat inwardly of the N-terminal of the heavy chain, these being points which are somewhat closer together in the natural antibody. The consequence of this is that a portion of the light chain adjacent its C-terminus and a portion of the heavy chain adjacent its N-terminus is not expressed and instead is replaced by the linking peptide. Even so the peptide link must be designed with some care so that it is of sufficient length to permit the two variable domains to fold and associate together.

EP-A-623679 which is a divisional out of EP-A-318554 also discloses the expression of a single polypeptide containing the binding portion of each variable domain along with a linking peptide sequence joining them together. The document teaches that the link should have a length of at least 10 amino acids, and mentions that the linking peptide could include a cleavage site recognizable by a site specific cleavage agent. It is stated that this could allow the $V_H$ and $V_L$ domains to be separated later, or the linker to be excised after folding at the binding site. The document does not elucidate how such a construct would be processed or utilised. However, it suggests that linking the $V_H$ and $V_L$ domains together may do little or no harm, and may even improve, binding properties.

Although the genetic constructs encoding single-chain Fv have some clear advantages in the production of antibody fragments, the resultant single-chain Fv protein is disappointing in its performance compared with the Fv fragments which have no link between the light and heavy chains. This is illustrated below by comparing the stability of the two different protein structures, stability being a very important performance criterion for industrial applications. Although single-chain Fv fragments are more stable than ordinary (two chain) Fv fragments when subject to prolonged storage at 37° C., we have observed that they are completely inactivated by some biophysical shocks such as a series of freeze/thaw cycles. In contrast, true (two-chain) Fv can survive freeze/thaw cycles with very little activity loss. A possible explanation for this extremely surprising discovery argues that the single-chain Fv is intrinsically more resistant to denaturation due to the covalent coupling of its two component domains (via the linker), therefore it can survive longer periods of storage at 37° C. than two-chain Fv; however, if the single-chain Fv is completely denatured by a biophysical shock, the presence of the linker interferes with the refolding process which would otherwise take place on a return to physiological conditions. In contrast, two-chain Fv can survive biophysical shocks by being denatured and then refold successfully. Whatever the explanation, antibody fragments intended for industrial applications should be robust enough to cope with perturbations likely to denature them such as elevated temperatures, freeze/thaw, or extremes of pH. A biophysical shock, sufficient to denature Fv may for instance be used to remove the Fv from an affinity column during purification. Consequently, the ability to refold spontaneously can be valuable. Also, single-chain Fv fragments have a tendency to give more non-specific binding, which is usually not desirable.

In the present invention, associative portions of a heavy chain and a light chain, e.g. the binding regions of their variable domains, are also expressed as parts of a single polypeptide in which they are connected through a linking peptide sequence. However, this connection incorporates a site for cleavage by an enzyme produced by the transformed organism which is expressing the polypeptide. After or during expression of the single polypeptide it is cut at the cleavage site while still within the culture where it has been expressed it, thereby detaching the portions of the heavy chain and the light chain from each other and allowing them to associate spontaneously together.

Thus the present invention provides a method of preparing an Fv antibody fragment or other product which incorporates associative portions of an antibody's light and heavy chains, by:

connecting nucleotide sequences which code for the portions of the two chains, by means of an additional nucleotide sequence which is interposed between them and which codes for a linking peptide sequence;

transforming a host organism to incorporate the connected nucleotide sequences;

culturing the transformed organism to express a polypeptide which contains the portions of the light and heavy chains, joined by a linking peptide sequence coded by the said additional nucleotide sequence;

characterised by inclusion of a cleavage site in the linking peptide sequence such that the linking sequence is cut enzymatically by an enzyme produced by the transformed organism.

It should thus be appreciated that in this invention the transformed organism synthesizes two peptide chains, both of which are desired, and both of which go into the final product, but initially they are joined, and are separated from each other by the organism after synthesis of the joint between them. The expressed, single polypeptide may exist for a short period as a transition state, or it is possible that cleavage will occur during the synthesis of its second chain. This can avoid difficulty if this single, expressed polypeptide would otherwise be toxic to the host organism.

Possibly the enzyme which carries out cleavage could be an enzyme occurring in the membrane of the transformed organism or even an extracellular enzyme that has been produced by the organism. In this event cleavage of the linking peptide would take place as the protein is excreted through the membrane or in the surrounding culture medium.

This method generally leads to a product in which at least one and probably both of the two portions of antibody chains is prolonged by a remnant of the linking peptide, although the remnant may be very small. It would be possible (although probably inconvenient) to design a linking peptide which is cut away completely This invention is particularly envisaged for the production of Fv fragments. The associative portions of the two chains will be their variable domains or at least the binding regions thereof. The product will then be an Fv antibody fragment in which at least one and probably both of the variable domains is attached to a remnant of is the linking peptide.

Because the peptide sequence which provides a link between the heavy chain variable domain and the light chain variable domain is cut after expression of the single polypeptide, there is greater freedom of choice in choosing the length of the linking peptide between them. Moreover there is no necessity to omit terminal portions of the desired variable domains for the sake of reducing the length of the link between them.

Although there is no need to omit terminal portions of the desired variable domains, this could nevertheless be done if desired. Generally the nucleotide sequences will code for at least the binding regions of antibody variable domains.

In one form of this invention, the link between the antibody chains is sufficiently short, e.g. less than 10 amino acids, that the two chains cannot associate together until the link is cut. The result of this is that (folded) single chain Fv is not produced as a transient product.

Nucleotide sequences which code for light and heavy chain variable domains can be obtained by cloning of existing genetic material. This can be done by means of the polymerase chain reaction (PCR) which is well known in the field of biotechnology. Literature references for this technique are:

Saiki et al, Science 230 1350 (1985)

Scharf et al, Science 233 1076 (1986)

and

Saiki et al, Science 239 487 (1988)

Its application to the cloning of variable domains has been described by Orlandi, Winter et al, PNAS USA 86 3833 (1989) and in EP-A-368684.

The essence of the PCR technique is repeatedly carrying out a cycle of steps comprising:

exposing a required nucleotide sequence in a nucleic acid strand, annealing a primer oligonucleotide adjacent an end of the required sequence, and synthesising a complementary nucleic acid strand extending from the primer, these steps being carried out utilising a primer able to anneal to one nucleic acid strand adjacent to one end of the requires sequence and a second primer able to anneal to the complementary nucleic acid strand adjacent the opposite end of the required sequence, thereby to produce clone strands of nucleic acid which are the required sequence with end-portions determined by the two primers.

A linking nucleotide sequence coding for the linking peptide can be made directly by oligonucleotide synthesis.

Assembly of the three nucleotide sequences to form an in-frame single nucleotide sequence can be carried out with standard techniques of recombinant DNA technology. In order to facilitate this it is preferred that the primers used in the PCR reaction provide restriction sites and that the linking nucleotide sequence also incorporate restriction sites.

Standard techniques of recombinant DNA technology can be used to transform a host organism with the nucleotide sequence.

A possibility is to transform the genetic material of the host organism so that it also expresses the protease enzyme which will recognise the cleavage site in the linking peptide.

In a development of this invention, the linking peptide is designed such that it incorporates a sequence of amino acids which can be used for recognition of the Fv fragments during assay and/or purification. Recognition of such a sequence would be utilised after cleavage, at which stage the recognition sequence should be present as a remnant of the linking peptide, attached to one chain of the Fv fragment.

In another development of this invention, the linking peptide sequence is designed such that it incorporates two cleavage sites. When the peptide sequence is cut at these sites, part of it is cut right out. Consequently the antibody fragment which is formed may carry only very small remnants of the linking peptide sequence, or no remnants at all.

Yeasts are presently preferred as organisms to be transformed and used to express the peptide chain, which is then cut. In particular methylotropic yeasts may be used, notably *Pichia pastoris* and the closely related *Hansenula polymorphia*.

The preferred proteases to cleave the linking peptide are of the KEX2-type. Enzymes of this group of proteases are found in many organisms. They recognise, and cleave ajacent to, a specific cleavage site of . . . Lys-Arg . . . provided that these are in an exposed position rather than concealed by folding of the peptide chain. Cleavage takes place next to arginine so that ... Lys-Arg-X- ...

is cleaved to

... Lys-Arg-COOH+H$_2$N—X ...

where X denotes any amino acid, and Arg-COOH indicates that after cleavage the arginine residue is as C-terminus.

Expression and cleavage into two peptide chains within the transformed organism will generally be followed by a step of harvesting or recovery in which the desired Fv fragments are separated from other constituents of the composition in which they have been formed. Notably, they will desirably be separated from the enzyme which brought about the step of cleavage. Techniques for the harvesting of biological molecules, such as polypeptides, are well known. Affinity chromatography is widely used.

The invention could be applied to the production of bodies in which the portions of the two chains are prolonged with further polypeptides. These could include the variable domains of the chains of a second antibody, thus leading to a product with two specific binding affinities, analogous to the diabodies described in Holliger et al PNAS 90 6444 (1993). Once again there would be the advantage that the required two polypeptides which associate together are made in equal amounts because they are expressed as a single polypeptide. In this case the two polypeptides which are linked should respectively contain at least one light chain and at least one heavy chain which will associate with it.

When this invention is applied to the production of diabodies, the linking peptide sequence which connects the polypeptides (and is eventually cut) may again be sufficiently short that association of the polypeptides does not take place until the link has been cut.

BRIEF DESCRIPTION OF THE DRAWINGS

Embodiments of the invention will be described by way of example, with reference to the accompanying diagrammatic drawings in which FIGS. 1 to 6 provide an illustration of the invention in principle, FIGS. 7 to 12 illustrate an example of the invention and FIGS. 13 to 17 illustrate the application of the invention to diabodies. More specifically:

FIG. 7 is a schematic representation of the construction of FvKC-II-KEX2 and Yeast-FvKC-II-KEX2 starting from FvKC-II.

FIG. 8 shows the nucleotide sequence (Seq ID No. 4) and corresponding amino acid sequence (Seq ID No. 5) of the FvKC-II genes on the HindIII-EcoRI fragment in pUC19.

FIG. 9 shows the nucleotide sequence (Seq ID No. 9) and corresponding amino acid sequence (Seq. ID No. 10) of the FvKC-II-KEX2 gene on the HindIII-EcoRI fragment in pUC19.

FIG. 10 shows the nucleotide sequence (Seq ID No. 13) and corresponding amino acid sequence (Seq. ID. No. 14) of the FvKC-II-KEX2 gene containing the 5' SnaBI restriction site on the HindIII-EcoRI fragment in pUC19.

FIG. 11 is a chromatrogram obtained when the protein produced in transformed Pichia cells was recovered by affinity chromatography.

FIG. 12 shows SDS-PAGE analysis of the eluted protein.

FIG. 13 illustrates a DNA sequence used to produce a diabody;

FIG. 14 shows the polypeptide coded by the DNA sequence of FIG. 13;

FIG. 15 shows the diabody obtained from the polypeptide of FIG. 14.

Figure 1:
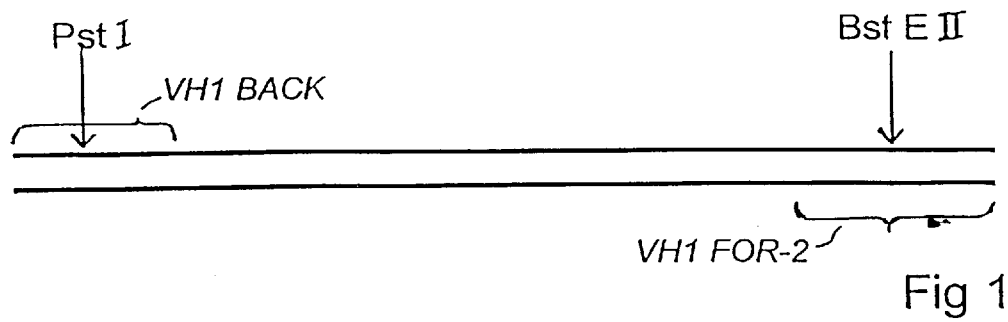
FIGS. 1 and 2 illustrate DNA sequences obtained by cloning.
Figure 2:
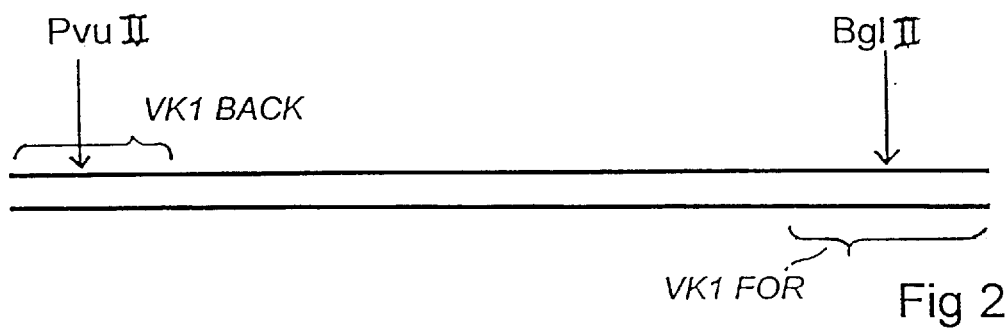
Figure 3:
FIG. 3 shows a sense strand of DNA, (Seq ID No. 1) made synthetically.

In the embodiment of the invention illustrated by FIGS. 1 to 3, the procedure commences with a hybridoma which produces a monoclonal antibody of the desired specificity.

The gene (DNA sequence) which codes for the heavy chain variable domain is cloned from the genome of this hybridoma by means of techniques described in Orlandi, Winter et al PNAS USA 86 3383 (1989) and EP-A-368684.

m-RNA is recovered from hybridoma cells and used to produce cDNA by reverse transcription. The desired gene is then cloned from this cDNA by means of the polymerase chain reaction. Suitable primers are $V_{H1}$ FOR2 and $V_{H1}$ BACK both disclosed in EP-A-368684.

The DNA produced in this way has a sequence corresponding to the $V_{H1}$ FOR2 primer at one end (the 5' end of the anti-sense strand) and a sequence corresponding to the $V_{H1}$ BACK primer at the 5' end of the sense strand. These sequences include Bst EII and Pst I recognition sites respectively.

The nucleotide sequence which codes for the light chain variable domain is cloned from the hybridoma genome in corresponding manner. When this is done, the primers used in the polymerase chain reaction are VK1 FOR and VK1 BACK as disclosed in EP-A-368684. The DNA which is produced in this cloning step has a sequence corresponding to the VK1 FOR primer at one end (the 5' end of the anti-sense strand). This includes a Bgl II recognition site. At the 5' end of the sense strand is a sequence coded by the VK1 BACK primer and including a Pvu II recognition site. This sequence is diagrammatically illustrated by FIG. 2.

A nucleotide sequence to code for a linking peptide is synthesised using standard techniques for oligonucleotide synthesis. For example, using an automated synthesiser, chemical reagents and protocols supplied by Applied Biosystems (Warrington, UK). The sequence has a Bst EII recognition site close to its 5' end. It has a Pvu II recognition site close to its 3' end. Intermediately between these two sites are a sequence of codons to produce a short linking peptide. In the sense strand these comprise a sequence ... CGA ATG GAT AAA AGG ... (Seq. ID. No. 1) which codes for ... Arg-Met-Asp-Lys-Arg ... (Seq. ID. No. 2). These five amino acids provide a protease cleavage site, as will be explained below. This nucleotide sequence is illustrated in FIG. 3 of the accompanying drawings.

Figure 4:
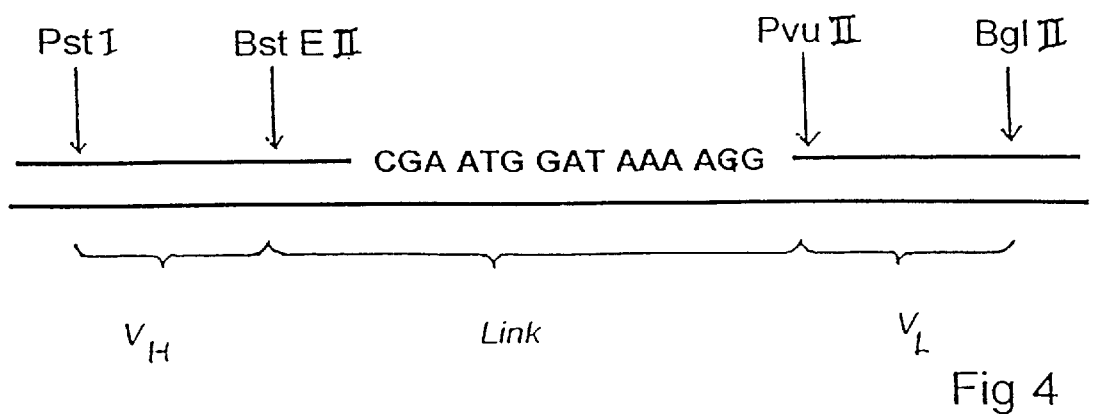
FIG. 4 shows a longer DNA sequence (Seq ID No. 1) obtained by ligating the sequences of FIGS. 1 to 3.

The three nucleotide sequences described above (and illustrated in FIGS. 1, 2 and 3 of the accompanying diagrammatic drawings) are then assembled, in-frame, to form a longer sequence in which the sequence coding for the linking peptide extends between the 5' end of the heavy chain sequence and the 3' end of the light chain sequence, as illustrated by FIG. 4.

The construction of a genetic cassette—i.e. an in-frame nucleotide sequence—with the design described above can be carried out by standard techniques of molecular biology. For instance Clackson et al—Nature 352 p. 624 (1991) especially p. 625—describes a suitable method, although without any cleavage site as here provided in the linking peptide.

The resulting nucleotide sequence, illustrated as FIG. 4, is preferably amplified further by the polymerase chain reaction and then inserted into a vector and used to transform a host organism.

The transformed organism is cultured and expresses a polypeptide containing the variable domains of the heavy and light chains, with the C-terminal of the heavy chain coupled to the N-terminal of the light chain variable domain through the linking peptide. This polypeptide is illustrated in FIG. 5.

Figure 5:
FIG. 5 shows the polypeptide coded by the DNA sequence (Seq ID No. 2) of FIG. 4.

The peptide link between the $V_H$ and $V_L$ fragments, as illustrated in FIG. 5, is short. It does not allow these fragments freedom of movement sufficient that they can associate together.

The chosen host organism can be the filamentous fungus, Aspergillus. An enzyme which naturally occurs within this organism is the KEX2 protease. As mentioned above, this protease functions to cleave a peptide chain adjacent to arginine in an exposed . . . -Lys-Arg-X- . . . sequence where X denotes any amino acid. KEX2-type enzymes are found in many different organisms. Once the polypeptide has been formed, it is cleaved by the KEX2 protease of the Aspergillus next to the -Lys-Arg- sequence of the linking peptide. Indeed, cleavage may occur after synthesis of one domain and the linking peptide, while synthesis of the second domain is in progress.

Figure 6:
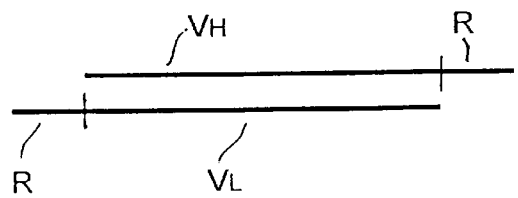
FIG. 6 shows an Fv fragment obtained from the polypeptide of FIG. 5.

The light and heavy chain variable domains can now associate together as diagrammatically illustrated in FIG. 6 and can fold into their natural shape. At the C-terminal end of the heavy chain variable domain, the peptide chain is prolonged by a fragment of the linker peptide. The remainder of this peptide prolongs the light chain variable domain at its N-terminal end. These remnants are indicated as "R".

Figure 7:
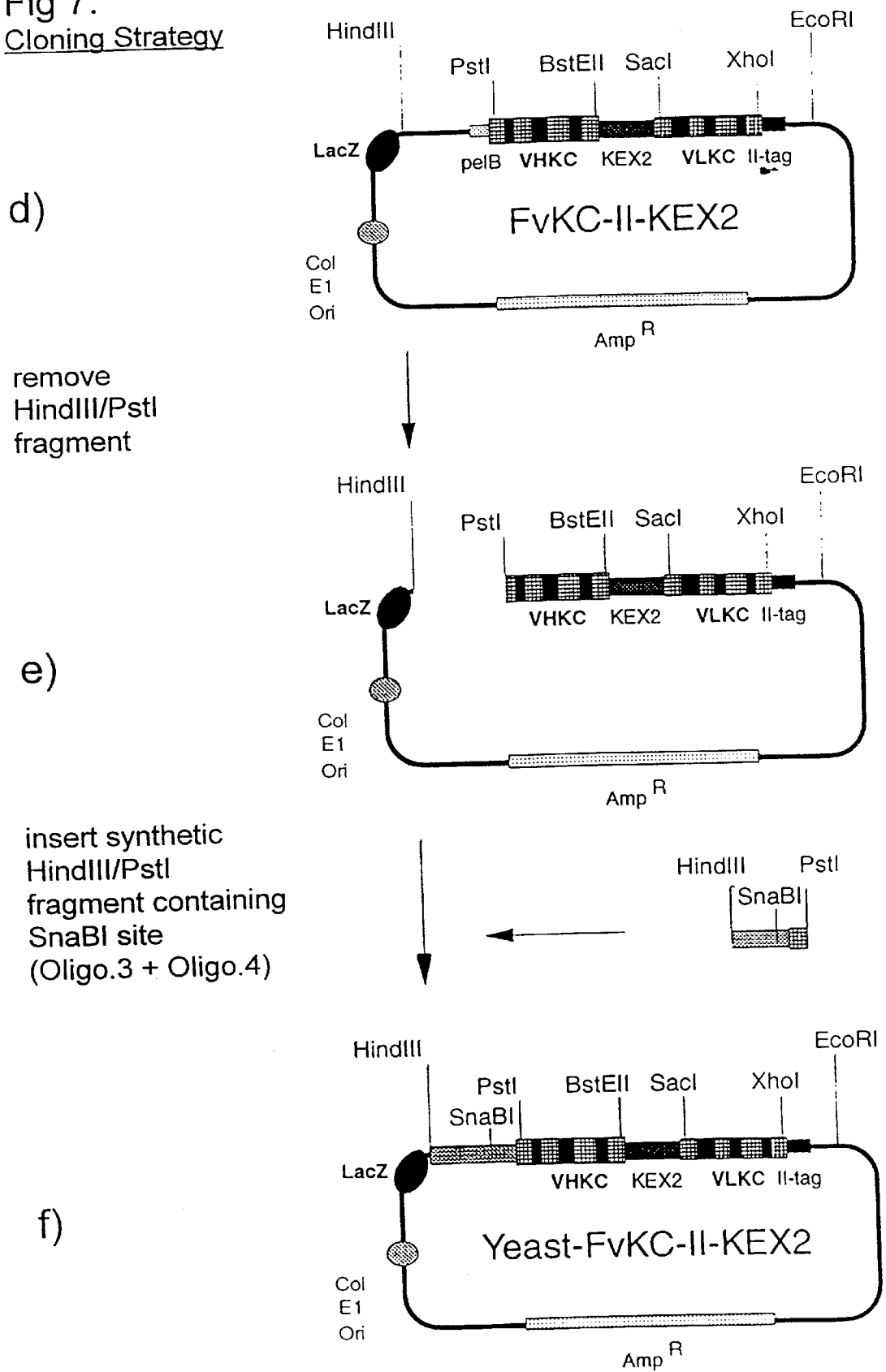

FIG. 7 illustrates, by way of example, the application of the invention to the production of an Fv (referred to as FvKC) which is specific for a peptide hormone. In this example, the producer organism is a methylotropic yeast, Pichia pastoris, which is known to produce a KEX2-type protease.

1) Generation of DNA construct coding for an Fv comprising a KEX2-type processing site (Arg-Met-Asp-Lys-Arg) positioned between the VH chain and the VL chain As shown in FIG. 7a, the DNA coding for an Fv (known as FvKC) with a specificity for a peptide hormone was assembled in an E. coli expression plasmid, pUC19, according to the method of Ward et al. Nature (1989) 341, 544. As in Ward's paper, the Fv was tagged at the C-terminus of its VL with a peptide tag (to facilitate assay of Fv activity). The peptide sequence (Seq. ID. No. 3) used in this example was the so-called hydrophil II tag (Gly-Ser-Gly-Ser-Gly-Asn-Ser-Gly-Lys-Gly-Tyr-Leu-Lys). This sequence was previously disclosed in Davis et al (1991) WO 91/08482. This starting DNA construct, shown in FIG. 7a, is designated FvKC-II. FIG. 8 shows the nucleotide sequence and corresponding amino acid sequence of the FvKC-II genes on the HindIII-EcoRI fragment in pUC19. The pelB leader and hydrophil-II tag sequences are shown in boxes. Relevant restriction sites are shown bold and underlined.

The FvKC-II DNA was amplified by growing it up in E. coli and recovering the plasmid DNA. The DNA between the $V_H$ and $V_L$ was removed by digesting with BstEII and SacI (as illustrated by FIG. 7b). This was then replaced (FIG. 7c) by a synthetic BstEII/SacI fragment encoding a KEX2-type cleavage site which was the Arg-Met-Asp-Lys-Arg sequence mentioned earlier. The synthetic fragment was composed of a pair of complementary oligonucleotides, Oligo 1 (Seq. ID No. 7) and Oligo 2 which were:

5'GTCACCGTCTCCTCACGAATG-
GATAAAAGGGACATCGAGCT'3            Oligo 1

5'CGATGTCCCTTTTATCCATTCGTGAGGAGACG'3   Oligo 2

The completed DNA construct was designated FvKC-II-KEX2. FIG. 9 shows the nucleotide sequence and corresponding amino acid sequence of the FvKC-II-KEX2 gene on the HindIII-EcoRI fragment in pUC19. The pelB leader, KEX2 site and hydrophil-II tag sequences are boxed. Relevant restriction sites are bold and underlined.

2) Introduction of FvKC-II-KEX2 DNA construct into a Pichia expression vector

The DNA construct FvKC-II-KEX2 was inserted into an expression vector (pPIC9) for production in the methylotrophic yeast, Pichia pastoris. To achieve this, the 5' end of the DNA construct had to be modified so that it contained a restriciton site that was compatible with the pPIC9 vector. (The restriction site SnaB1 was chosen). This modification was made by removing a HindIII/PstI fragment and replacing it with a synthetic HindIII/PstI fragment that contained a SnaBI site. (Refer to FIGS. 7d, e and f). The synthetic fragment was composed of a pair of complementary oligonucleotides, Oligo 3 (Seq. ID No. 11) and Oligo 4 (Seq. ID No. 12) which were:

5'AGCTTACGTACAGGTGCAGCTGCA 3'      Oligo 3

5'GCTGCACCTGTACGTA 3'              Oligo 4

The completed DNA construct was designated Yeast-FvKC-II-KEX2. FIG. 10 shows the nucleotide sequence and corresponding amino acid sequence of the FvKC-II-KEX2 gene containing the 5' SnaBI restriction on the HindIII-EcoRI fragment in pUC19. The KEX2 site and hydrophil-II tag sequences are in clear boxes; the Sna BI and EcoRI restriction sites are in grey boxes. Other relevant restriction sites are bold and underlined.

The Yeast-Fv-II-KEX2 construct was amplified by growing in pUC19/E. coli. The construct was excised from plasmid pUC19 by digestion with SnaBI and EcoRI. (EcoRI is naturally present at the 3' end of the construct (refer to FIG. 7f).) The excised DNA was then ligated into the Pichia expression vector, pPIC9. [This vector is a component of the Pichia expression kit (version B), supplied by Invitrogen Corporation, San Diego, USA.]

3) Production and recovery of active FvKC-II from Pichia

The pPIC9 DNA with the insert of Yeast-Fv-II-KEX2 was linearised by digesting with BglII. Then Pichia pastoris strain GS115 was transformed with this DNA according to the instruction manual supplied with the Pichia expression kit (version B).

500 mls of transformed Pichia culture was produced according to the instruction manual. This was then centrifuged and induced to express FvKC-II in a volume of 100 mls, again according to Invitrogen's instruction manual. After 48 hours of induction, cells were removed by centrifugation. 60 mls of the supernatant was loaded onto an affinity chromatography column comprising the peptide hormone (to which FvKC binds) immobilised on CNBr-activated SEPHAROSE4B (Pharmacia). After loading the column, the adsorbent was washed with phosphate buffered saline (PBS) and then with 1 column volume of 1M sodium chloride (to eliminate non-specific binding). Bound (and therefore active) Fv was recovered by eluting with 50 mM glycine, pH2.2 Elution from the column was detected by uv absorption. The chromatogram is shown at FIG. 11.

Recovered fractions were neutralised with tris buffer and then dialysed into PBS. Two fractions were taken (refer to FIG. 11). Fraction 1 had a volume of 2 mls and contained 36 µg/ml protein. Fraction 2 had a volume of 4 mls and contained 78 µg/ml protein. Fractions 1 and 2 were analysed by SDS-PAGE. This was conducted with five lanes which were 1. Pharmacia low molecular weight markers;
2 Fraction 1;
3. Fraction 2;
4. Single chain Fv of the same hormone, expressed in *E. coli;*
5. A mixture of single chain Fv and the separate $V_H$ and $V_L$ chains, all expressed in *E. coli.*

The result of SDS-PAGE is reproduced as FIG. 12. It can be seen that for both lane 2 and lane 3, there were equal quantities of the two protein chains $V_H$ and $V_L$. There was negligible single chain Fv, nor were there fragments of lower molecular weight which would come from (unwanted) random cleavage of the peptide chains.

As neither of these chains can bind the peptide hormone on their own (they can only bind when associated in the form of an Fv), it is clear that the Pichia had synthesised VH-KEX2-VL-II; that this protein had been cleaved to yield equal amounts of VH and VL-II; and these two chains had associated to produce active Fv therefore being applied to the affinity column. The Fv dissociated into separate chains when eluted from the column and was detected as separate chains by SDS-PAGE.

Figure 13:
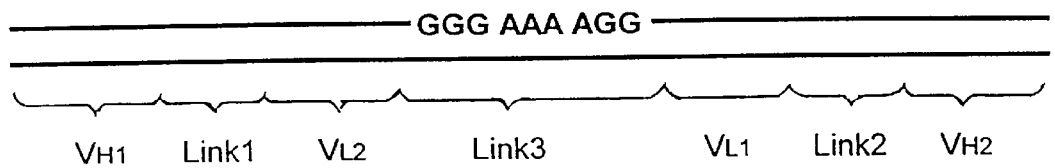
Figure 14:
Figure 15:
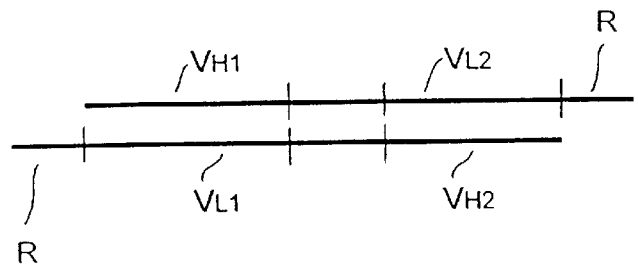

FIGS. 13 and 14 illustrate the utilisation of this invention in the production of a diabody as illustrated by FIG. 15. This is an artificial construction containing the variable domains of one antibody ($V_{H1}$ and $V_{L1}$) and the variable domains ($V_H2$ and $V_L2$) of a second antibody so that the artificial construct will display specific binding affinity for two different epitopes.

To make this construct, utilising this invention, nucleotide sequences coding for each of the heavy chain variable domains and each of the light chain variable domains are cloned in the manner described previously. These are assembled in the arrangement shown by FIG. 13.

As indicated in this figure, the overall nucleotide sequence includes at one end the nucleotide sequence which codes for the heavy chain variable domain of one antibody ($V_{H1}$) and the nucleotide sequence which codes the light chain variable domain of the second antibody ($V_{H2}$) These nucleotide sequences are connected through a synthetic oligonucleotide sequence designated as link 1. The manner of assembling these nucleotide sequences can be generally as described previously but the link 1 sequence must not code for any protease cleavage site. Suitably it contains only glycine and serine.

The nucleotide sequence coding for the light chain of the variable domain of the first antibody ($V_{L1}$) is similarly connected through a synthetic nucleotide sequence, designated link 2, to the nucleotide sequence which codes for the variable domain of the heavy chain of the second antibody ($V_{H2}$).

The sequences coding for each of the light chain variable domains are connected through a linking sequence indicated as link 3 which codes for a peptide sequence which does contain a cleavage site. Link 3 is here exemplified as coding for . . . Gly-Lys-Arg . . . but it may code for some other peptide link containing a suitable cleavage site. When all of these nucleotide sequences have been assembled, the resulting sequence is incorporated into a host organism which is cultured to express the polypeptide shown by FIG. 14. This is then brought into contact with protease which functions to sever the link 3 amino acid sequence but not link 1 or link 2. The resulting two polypeptides are now able to associate together to give the diabody illustrated by FIG. 15. Remnants "R" of the central link 3 peptide extend from the N-terminal of $V_{L1}$ and the C-terminal of $V_{L2}$.

We claim:

1. A method of preparing a proteinaceous product which incorporates associative portions of antibody light and heavy chains, by:
   connecting nucleotide sequences which code for the portions of the two chains, by means of an additional nucleotide sequence which is interposed between them;
   transforming a host organism to incorporate the connected nucleotide sequences;
   culturing the transformed organism to express a polypeptide which contains the portions of the light and heavy chains, joined by a linking peptide sequence coded by the said additional nucleotide sequence;
   characterised in that a cleavage site in the linking peptide sequence is such that this linking peptide is cut enzymatically by an enzyme produced by the transformed organism followed by recovery of the proteinaceous product,
   wherein the linking peptide which joins the portions of the light and heavy chains is too short to allow the portions to associate with each other before the linking peptide is cut.

2. A method according to claim 1 wherein the genetic material of the host organism is transformed to express the protease as well as being transformed to express the said polypeptide.

3. A method according to claim 1 wherein the associative portions of the two chains include at least the antigen binding regions of the variable domains of the light and heavy chains.

4. A method according to claim 1, wherein the associative portions are the variable domains of the light and heavy chains of a single antibody so that the product of the method is an Fv antibody fragment.

5. A method according to claim 1, wherein the associative portions are the variable domains of the light and heavy chains of two antibodies so that the product of the method is a diabody incorporating two Fv antibody fragments.

6. A method according to claim 1 incorporating a purification step carried out by binding a support to a sequence of amino acids of the linking polypeptide.

7. A method according to claim 1 accompanied by an assay step carried out by binding a support to a sequence of amino acids of the linking polypeptide.

8. A method according to claim 1, wherein the linking peptide contains more than one cleavage site and exposure of the polypeptide to the said enzyme entirely detaches the part of the link between the two cleavage sites.

9. A method according to claim 8 wherein the protease is of the KEX2 type.

10. A method according to claim 8, wherein the enzyme to cut the linking peptide sequence is a protease.

11. A method according to claim 10 wherein the protease cuts the linking peptide between arginine and an adjacent amino acid X in a sequence . . . lysine-arginine-X . . .

where X denotes any amino acid.

12. A method according to claim 1 wherein the transformed organism is a yeast.

13. A method according to claim 12 wherein the transformed organism is a methylotropic yeast.

* * * * *